United States Patent [19]

Feimer

[11] Patent Number: 5,015,241
[45] Date of Patent: May 14, 1991

[54] SAFETY SYSTEM FOR HYPODERMIC SYRINGE AND NEEDLE

[76] Inventor: Michael P. Feimer, 13627 Hascall, Omaha, Nebr. 68114

[21] Appl. No.: 484,504

[22] Filed: Feb. 26, 1990

Related U.S. Application Data

[63] Continuation-in-part of Ser. No. 208,682, Jun. 20, 1988, Pat. No. 4,915,696.

[51] Int. Cl.[5] ............................................. A61M 5/32
[52] U.S. Cl. ..................................... 604/198; 604/263
[58] Field of Search ............... 604/110, 192, 198, 195, 604/187, 263

[56] References Cited

U.S. PATENT DOCUMENTS

| | | | |
|---|---|---|---|
| 2,571,653 | 10/1951 | Bastien | 604/198 |
| 2,674,246 | 5/1954 | Bower | 604/198 |
| 4,425,120 | 1/1984 | Sampson | 604/198 |
| 4,573,976 | 3/1986 | Sampson | 604/198 |
| 4,631,057 | 12/1986 | Mitchell | 604/198 |
| 4,655,751 | 4/1987 | Hasbaugh | 604/198 |
| 4,659,330 | 4/1987 | Nelson | 604/192 |
| 4,664,654 | 5/1987 | Strauss | 604/198 |
| 4,666,435 | 5/1987 | Braginetz | 604/198 |
| 4,681,567 | 7/1987 | Masters | 604/198 |
| 4,693,708 | 9/1987 | Wanderer | 604/198 |
| 4,702,738 | 10/1987 | Spencer | 604/198 |
| 4,798,587 | 1/1989 | Willoughby | 604/110 |

FOREIGN PATENT DOCUMENTS 2201094 8/1988 United Kingdom ................ 604/110

Primary Examiner—John D. Yasko
Attorney, Agent, or Firm—James D. Welch

[57] ABSTRACT

A simple, economical, easy to manufacture and use system for protecting against unintended pricks from used hypodermic syringes and needles, and the leakage of fluid therefrom is disclosed. The system involves an assembly for attachment to standard syringe, barrels, which assembly comprises a guide, a needle securing plunger which fits into the guide and means for attaching the assembly to a syringe barrel. Provision to prevent the needle securing plunger from falling out of the guide is included, as are needle securing plunger design considerations which serve to ensure the needle securing plunger will allow embedding a needle in a needle pocket at the end of the needle securing plunger, and which serve to provide natural spring from interaction of the guide and the needle securing plunger when the end of the needle securing plunger, (i.e., the needle pocket region), is in place over a needle tip. Additionally, a preferred packaging system to assure sterility and allow easy identification of needle or syringe length or gauge, etc. is disclosed. Also taught, are the methods of use of the system to both protect and re-expose a hypodermic needle point, and for disposing of a used assembly into a container.

2 Claims, 2 Drawing Sheets

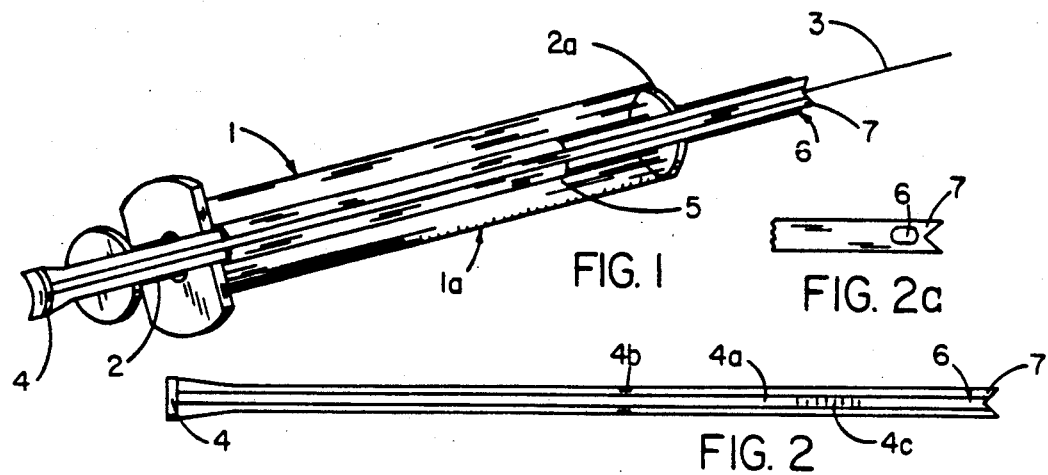
FIG. 1
FIG. 2a
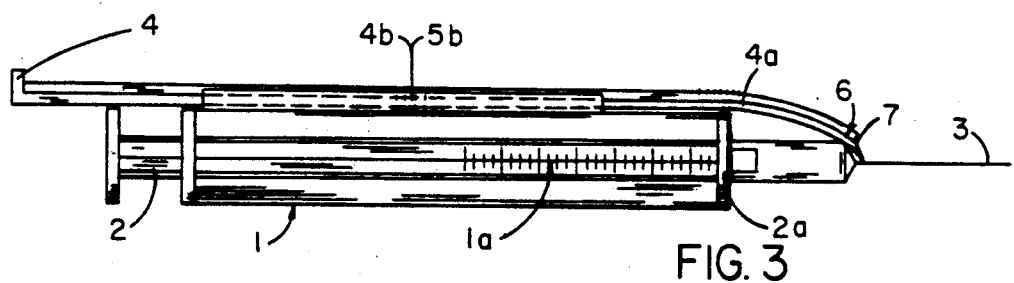
FIG. 2
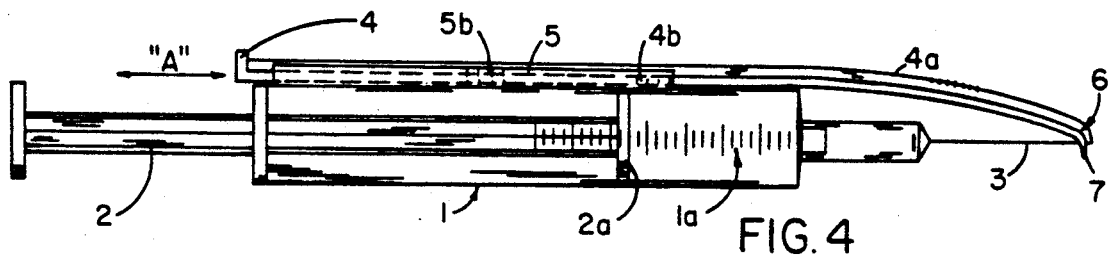
FIG. 3
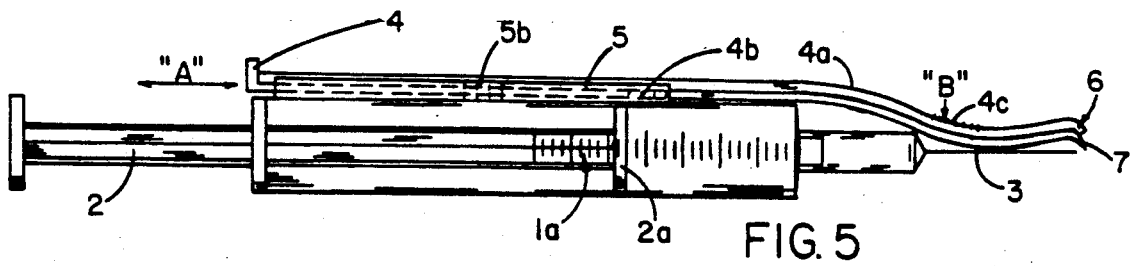
FIG. 4
FIG. 5
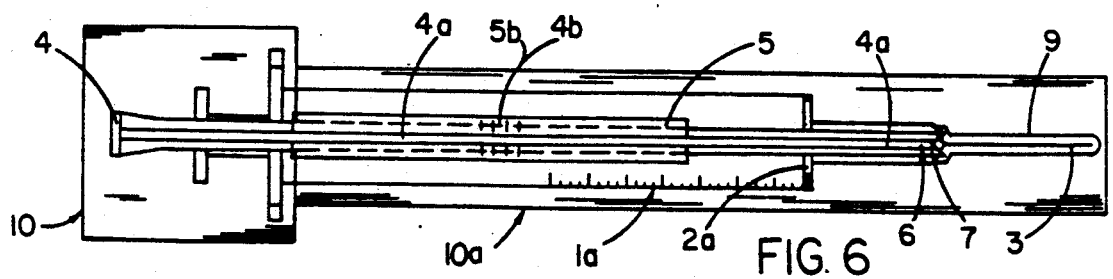
FIG. 6

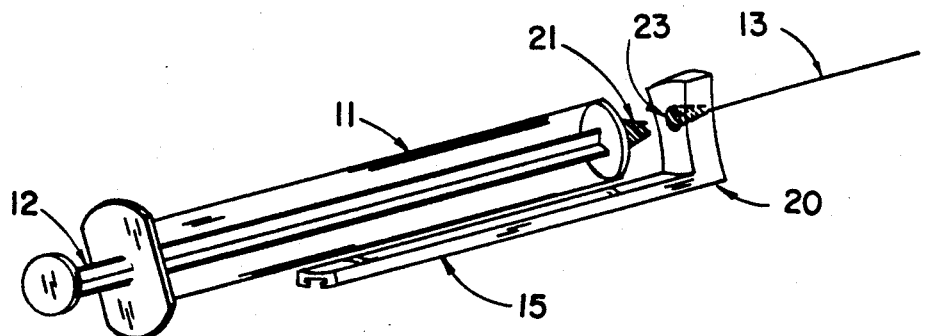
FIG. 7
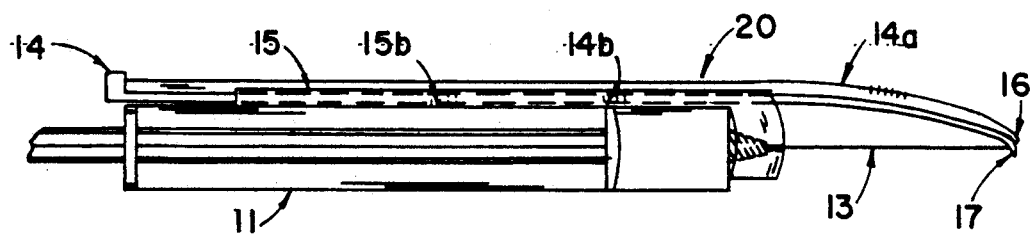
FIG. 8
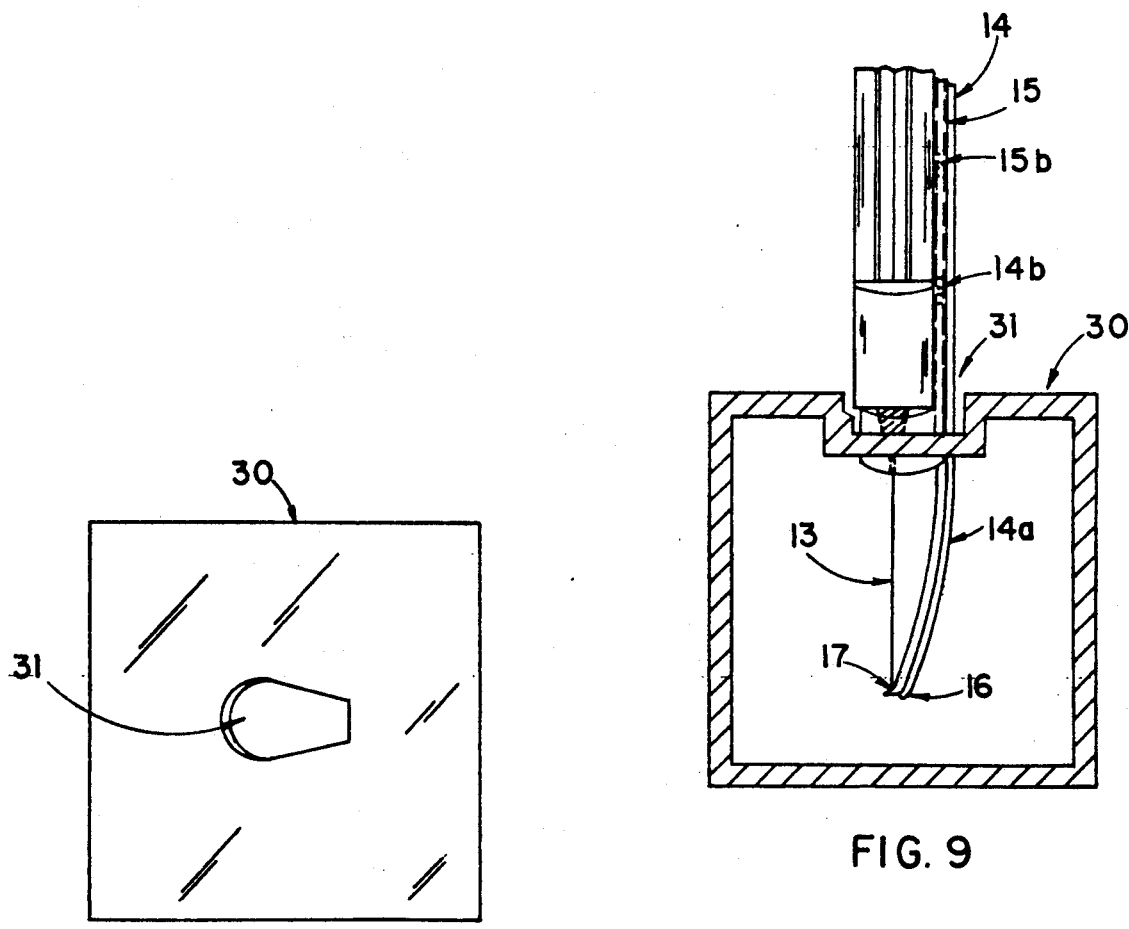
FIG. 9
FIG. 10

SAFETY SYSTEM FOR HYPODERMIC SYRINGE AND NEEDLE

The subject matter of this application was disclosed in Disclosure Document No. 183,179. This application is a continuation-in-part of U.S. application Ser. No. 07/208,682 filed June 20, 1988, now U.S. Pat. No. 4,915,696.

TECHNICAL FIELD

The present invention pertains generally to hypodermic syringes and needles and more particularly, the present invention focuses on a system with provision for protecting a needle attached to a syringe after the combination has been used to prevent accidental "pricking" of unintended persons, and to prevent unintended fluid leakage from the syringe. The present system is simple to use and easy to manufacture.

BACKGROUND

Hypodermic syringes and needles are used for injections and drawing blood in medical and veterinary settings throughout the world. In health care settings large numbers of patients require injections or blood sampling services in short periods of time. The use of large numbers of hypodermic syringes and needles under the constraints imposed by typical health care environments, inevitably, leads to health care professionals accidentally pricking themselves, or others with a previously used needle, or alternatively, coming into contact with fluids which have leaked from a syringe, the needle associated with which was not capped after use. The recent AIDS epidemic has heightened awareness of the potentially devastating effect such accidents can have. Not only can patients become mortally infected by a needle prick, or contact with fluid leaked from a syringe but health care professionals can as well. A needle prick can end the career of a health care professional, which career took years to nurture, in but a second. The inevitable nature of such occurrences has led creative people to design new systems and propose methods of use of specialty hypodermic syringes and needles, or adaptations thereof, which have as their focus the minimization of the risk that unintended needle pricks and/or fluid spills from used systems with uncapped needles will occur.

In recent years a number of patents have issued, the inventions in which teach means by which the risk alluded to can be lessened. In evaluating said inventions, a number of factors must be considered. The foremost factor is, of course, the likelihood of success in achieving a lessened risk of unintended needle pricks and/or fluid spills from used systems. Generally, such likelihood is reduced in inverse proportion to the level of difficulty involved in practicing the system or method of a given invention. The more difficult it is to use an invention, the less likely it is to be successful or even used. Another consideration is the complexity of an invention per se. Accompanying complexity is the consideration of the cost of manufacturing an invention.

An ideal system for lessening the risk of accidental needle pricks and fluid spills from used syringes would be very easy and economical to manufacture and extremely simple to use.

A study of existing prior patents in relevant areas show that many prior inventions which provide means for securing a needle after use, are complex to manufacture (hence potentially expensive) and/or operate, (e.g., 4,631,057 to Mitchell; 4,425,120 to Sampson; 4,666,435 to Braginetz; 4,664,654 to Strauss; 4,693,708 to Wanderer; 2,674,246 to Bower; 4,681,567 to Masters; 4,655,751 to Harbaugh; and 4,702,738 to Spencer).

A study of existing patents in the relevant area also shows that many prior inventions which provide means of securing a needle after use require two hands to use effectively, (e.g., 4,631,057 to Mitchell; 4,573,976 to Sampson; 4,425,120 to Sampson; 4,666,435 to Braginetz; 4,659,330 to Nelson; 4,693,708 to Wanderer; 4,681,567 to Masters; 4,655,751 to Harbaugh; 4,702,738 to Spencer; and 2,571,653 to Bastien). The necessity of using two operate a mechanism is a definite drawback. An ideal mechanism should be easy to operate with one hand, perhaps by motion imparted by a user's thumb as a syringe rests on the surface formed by the fingers of the same hand.

Some prior inventions involve a needle guard which must be rotated to be used, (e.g., 4,425,120 to Sampson; 4,666,435 to Braginetz; 4,693,708 to Wanderer; 2,674,246 to Bower; 4,702,738 to Spencer). In addition, some needle guards are free to rotate around a syringe even though rotary motion is not required for operation (e.g., 4,631,057 to Mitchell; 4,573,976 to Sampson; 4,655,751 to Harbaugh; 2,571,653 to Bastien). It is not necessary to protect a needle point that a shield rotate, rather a shield must move longitudinally along a needle to accomplish the task. It is doubtful if any benefit provided by the rotational aspect of the shield justifies the added complexity in construction, and potential for blocking the ability to observe the contents of a syringe by the rotational motion of the shield. Further examination of existing patents show that view of liquid in a syringe taught in said patents is by way of two layers of plastic or glass, (e.g., 4,631,057 to Mitchell; 4,573,976 to Sampson; 4,425,120 to Sampson; 4,666,435 to Barginetz; 4,693,708 to Wanderer; 2,674,246 to Bower; 4,681,567 to Masters; 4,655,751 to Harbaugh; 4,702,738 to Spencer; and 2,571,653 to Bastien). Any obstruction of view in addition to a syringe wall, of the liquid in a syringe is an undesirable factor. Such obstruction simply serves no useful purpose.

Further study of existing patents show some inventions require springs in their construction (e.g., 4,664,654 to Strauss; and 2,674,246 to Bower). Springs are added complexity and it would be preferable if any "spring" required could be a natural consequence of the design of an inventions parts so as to include such naturally, perhaps in the form of molded plastic parts with physical "memory".

Many existing inventions also provide needle shields which are open at their end. That is the needle is inside a tubular structure or equivalent which is not closed at its end. Examples are the inventions in Patent Nos. 4,631,057 to Mitchell; 4,573,976 to Sampson; 4,425,120 to Sampson; 4,666,435 to Braginetz; 4,664,654 to Strauss; 4,693,708 to Wanderer; 4,681,567 to Masters; 4,655,751 to Harbaugh; and 2,571,653 to Bastien). Two inventions provide caps to cover open ended needle shields, (e.g., 2,674,246 to Bower and 4,702,738 to Spencer). Except for these inventions, all those with open ended needle shields can allow fluid to leak out of a syringe. The obvious disadvantage of such is that one could come into contact with fluid which has leaked from a syringe and be infected through a pre-existing wound. A safe needle guard should provide for preventing leakage from a syringe without requiring a dangerous recapping process in which two hands are required to perform.

It should also be noted that of the inventions alluded to, only that in Patent No. 4,664,654 to Strauss does not require that a collar be placed around the syringe itself to achieve its system, and only the invention in Patent No. 4,681,587 to Masters provides for a clear syringe when the needle shield is mounted on a syringe. Both inventions require two hands to operate as well.

A system which would provide for securing syringe needles to prevent accidental needle pricks and which would prevent fluid leakage from syringes when in place (i.e., closed end on needle when in place), and which would provide clear view of fluid in a syringe through one layer (i.e., no collar required on a syringe) of plastic or glass both prior to and after securing a needle; and which provides spring to ensure needle securement by clever design of elements rather than by use of springs per se; and which does not require, or even allow, needle guard rotation; or require more than one hand to operate; and which is simple and economical to manufacture would be of great utility. Such a system is taught herein, directly.

DISCLOSURE OF THE INVENTION

The need for a noncomplex, economic and easy-to-use system which secures used syringe needles to prevent accidental pricking of unintended patients and medical professionals, etc. as well as prevent liquid leakage from a used syringe, while providing a clear view of liquid in the syringe, is met by the present invention. The method of the present invention provides for one-handed operation and the system is designed so that spring action is accomplished without the use of springs per se. The spring action serves to ensure against a needle, once secured, from inadvertently becoming again free.

The system of the new invention, in one embodiment, comprises a syringe barrel to which is longitudinally attached a guide. The guide provides for a plunger, which plunger fits into and slides within the guide. The plunger extends beyond the guide at both the needle and syringe end of the guide. At the syringe end, the plunger is constructed to allow a user's thumb or finger, etc. to press thereon and cause the plunger to move in the guide, thereby causing the end of the plunger at the needle end of the guide to extend further beyond the guide. The plunger is fabricated so that it has a will to bend toward the needle as it leaves the guide. This bending action causes the plunger to contact the needle and ride along it in a v-shaped groove in the tip of the plunger until it reaches the end of the needle, at which time it bends over the tip of the needle. Simultaneously, at the opposite, syringe, side of the guide, the plunger is constructed so as to flare out. That is the plunger becomes slightly wider and, hence, more difficult to press into the guide. When a person removes his or her thumb or finger from the syringe side of the plunger, the plunger has a natural "spring" or recoil tendency which causes the plunger to move slightly back toward the syringe side of the guide. Because, however, the tip of the needle has already been covered by the opposite, needle, side of the plunger, the needle is caused to insert slightly into the plunger at the point of the needle-plunger contact. The plunger at that point contains a pocket to aid this action and enhance the effect. The result of the above described action is that a needle is secured. The plunger then acts as a guard against accidental pricking of patients, medical personnel, etc., and it also acts as a plug to prevent liquid from leaking from the syringe through the needle.

Provision is made, preferably by constructing the plunger and guide with teeth on the outside of the plunger and teeth on the inside of the guide, to prevent a plunger from falling back out of the guide prior to use. That is, once a plunger is inserted into a guide to its pre-use position, it cannot be easily pulled back out. It can be easily pushed toward the needle, however, when it is desired to secure the needle.

Should it be necessary to remove liquid from a syringe intentionally, the plunger can again be pushed forward so that the needle point is no longer embedded in the pocket therein at the point where the needle contacts the plunger. By then applying pressure on the plunger between the point at which it leaves the guide and the location of the needle point (note this is safely away from the needle point itself) in the direction of the needle, and perhaps slightly, back toward the syringe barrel, the plunger is caused to move away from the tip of the needle. The pressure applied to the plunger at the head syringe side thereof can then be released and the needle tip thereby becomes re-exposed. Note that simply releasing pressure at the syringe side of the plunger will cause it to naturally retract due to the flare out widening of the plunger at the entrance of the guide at the syringe side.

The present invention, in its first embodiment, requires that syringes have permanently attached needles and that specific plungers be used in conjunction with specific length needles and syringes, so that proper coordination occurs during use. The syringes, with permanently attached needles and plunger-guide system are meant for one-time only use.

The guide and plunger are of relatively small width compared to the circumference of the syringe barrel, hence, do not significantly reduce or obstruct view of liquid inside the syringe.

In a second embodiment the plunger guide is connected to an assembly to which is also connected the needle and a means for connecting the assembly to a hypodermic syringe barrel. That is the plunger guide does not attach to the barrel of the hypodermic syringe. The second embodiment operates in the same way the first embodiment operates, but in addition provides for removal of the assembly from the syringe barrel after use. That is, the needle, secured by a needle securing plunger which is slid into the plunger guide on the assembly, can, with the entire assembly, be removed from the syringe barrel after use. An additional element, a container, can be provided to aid with the removal. The container is fitted with a hole shaped so that when an assembly is placed therein, the assembly cannot rotate. A simple rotation of the syringe barrel then effects removal of the assembly which is typically connected to the syringe barrel by means exemplified by screw threads.

SUMMARY OF THE INVENTION

Hypodermic syringes and needles are used for injections, and the drawing blood, in medical and veterinary settings throughout the world. The recent AIDS epidemic has heightened awareness of the danger accidental needle pricks from used needles present to patients and medical professionals, etc. Numerous patents have taught inventions which have as their purpose the prevention of unintended needle pricks. A study of relevant prior patents, however, shows that no prior invention intended to prevent accidental needle pricks and provides a simple economical system for securing syringe needles which system comprises a guide and plunger mechanism with natural needle setting spring, which system prevents leakage from a secured needle, but which system simultaneously allows unobstructed view of liquid inside an associated syringe and which system provides for a method of use which requires only one hand to practice.

The present invention comprises a syringe with (in one embodiment) a permanently attached needle, to the barrel of which syringe is attached a guide, into which guide a plunger is placed. At the needle end of the plunger, facing the needle, is located a pocket structure, and at the syringe end of the plunger is located a structure via which a person can place pressure with his or her thumb while the syringe is held in the fingers of the same hand. The plunger, at the needle end, is constructed with a tendency to bend toward the needle, and at the syringe end, a flare out increased width is present. The method of operation comprises applying pressure on the plunger at the syringe end so that the plunger slides toward the needle and curves to contact said needle until reaching and extending over the tip of the needle. The pocket in the needle end of the plunger serves to encompass the tip of the needle, and when pressure is released at the syringe end of the plunger, the plunger tends to naturally retract as a result of the flared out width of the plunger at the point it enters the guide. It is important to note, in the present invention, that the plunger be of a proper length to accommodate the needle permanently attached to the syringe, hence, different length plungers will be required for different length needles. The invention also provides means to prevent the plunger from sliding back out of the guide after it is placed in the guide in its pre-use position.

A second embodiment of the invention provides an assembly which comprises a means for connection to a syringe barrel, a syringe needle and an attached guide for a needle securing plunger. That is, the guide does not attach to the barrel of the hypodermic syringe as it does in the first embodiment. The second embodiment allows easy and safe removal of the assembly after use, once the needle has been secured by a needle securing plunger which slides into the guide.

Finally, the entire syringe and needle will be packaged so that the syringe, needle and needle guard apparatus can be kept sterile until intentionally opened. The packaging will be designed with colors to code for the length or gauge of the needle or syringe size, etc.

A purpose of the present invention is to provide a safe, easy to manufacture and easy to use system for protecting against unintended needle pricks and/or spilled fluid by or from respectively a used hypodermic syringe and needle combination.

BRIEF DESCRIPTION OF THE DRAWINGS

FIG. 1 is a perspective view of a syringe with the present invention incorporated therein.

FIG. 2 is a top view of the needle securing plunger.

FIG. 2a is a partial view of the bottom of the needle securing plunger.

FIG. 3 is a side elevational view of a syringe with the present invention incorporated therein, in a pre-use position.

FIG. 4 is a side elevational view of a syringe with the present invention incorporated therein, in a post-use (after drawing blood for instance) position.

FIG. 5 is a side elevational view of a syringe with the present invention incorporated therein, in a post-use position, but manipulated to re-expose a needle tip so fluid in the syringe can be intentionally removed.

FIG. 6 is a top planer view of a syringe with the present invention incorporated therein, in a sterile container.

FIG. 7 is a perspective view of a second embodiment of the present invention in which the plunger guide and needle are combined into a single separate assembly, which assembly also comprises means for connection to a syringe barrel.

FIG. 8 is a partial side elevational view of the second embodiment showing the assembly connected to a syringe barrel, and showing the needle secured by the invention.

FIG. 9 is a cross sectional side elevational view of a container structure with a used second embodiment of the invention entering from the top thereof, into which container the plunger guide and needle assembly can be disposed of.

FIG. 10 is a top view of a container for disposal of the plunger guide and needle assembly of the second embodiment of the invention, showing the opening into which the assembly is placed and secured while the syringe barrel is rotated to disconnect it from the assembly.

BEST MODES FOR CARRYING OUT THE INVENTION

Turning now to FIG. 1, there is shown a perspective view of a syringe barrel (1), a needle (3) and a syringe plunger (2), all said elements being essentially identical to the elements in standard syringes which are available off the shelf from medical and veterinary supply houses. Shown as well is a scale (1a) on the syringe barrel (1) which is easily viewed by someone using the syringe.

Also shown in FIG. 1 or in FIGS. 2 and 3 is a guide (5) and needle securing plunger (4), (4a), (4b), (6) and (7) (herein after referred to as the NSP). The NSP slides into the guide (5) until the teeth (4b) on the NSP, and teeth on the inner sides of the guide (5) identified as (5b) (in FIG. 3) mesh. This position is a "pre-use" position and the teeth (4b) and (5b) prevent the NSP from falling out of guide (5) once the NSP is in said "pre-use" position. The NSP has a head portion (4), a shank portion (4a), which shank portion can include ribbing identified as (4c), a needle pocket portion (6) and a needle guide structure portion (7), in addition to the teeth (4b). Note that the guide (5) can have any inner lateral wall shape, and the NSP a complimentary shape, which causes the NSP to remain in the guide (5). Any complimentary shapes for guide and plunger can be used.

FIG. 2 shows a top view of the NSP separate from the guide (5). Note the NSP narrows as one progresses from the head portion (4) toward the shank portion (4a). FIG. 2a shows the forward portion of the underside of NSP. In particular note the needle pocket (6).

FIG. 3 shows a side elevational view of the syringe barrel (1), needle (3), syringe plunger (2), guide (5), and NSP in a pre-use position. Pre-use as used here assumes the hypodermic will be used to draw blood. The hypodermic syringe plunger (2) would be extended as shown in FIGS. 4 and 5 if the use is to be for an injection, and post-use would show the syringe plunger (2) pushed into the syringe barrel (1). Note that the liquid measuring scale (1a) is unobstructed and liquid can be easily viewed through the single wall of the syringe barrel (1).

FIG. 4 shows a syringe after it has been used to draw blood. Note the end of the syringe plunger (2a) is visible through scale (1a), which scale is printed on the syringe barrel (1) directly. FIG. 4 also shows the NSP has been pushed toward the needle (3) by a force "A" applied at the NSP head (4). This has caused the needle guide structure (7) to make contact with the needle and guide the needle pouch (6) over the needle tip. The needle guide structure (7) curves to the needle as a result of spring placed in the NSP material during manufacture. Any material which tends to "remember" its shape can be used to fabricate the NSP and provide this attribute.

When force "A" is released the NSP will have a tendency to pull-back and, hence, secure the needle tip in the needle pocket (6) against accidental leakage and unintended pricking of patients, medical professionals, etc. The reason that the NSP will tend to pull back is that the NSP is wider near the head (4) than it is at the shank (4a). The guide (5) will attempt to prevent the wider portion of the NSP from remaining therein, as a result. This is another use of natural spring resulting from clever design of a minimal number of invention elemental parts.

FIG. 5 demonstrates that should one wish to reopen the tip of the needle, say to intentionally release the fluid in the syringe, the act can be accomplished safely. A force, indicated as "A" is applied to the NSP head (4) and a force shown as "B" is simultaneously applied to the NSP shank (4a) thereby causing the needle pocket (6) to move away from the tip of the needle. Ribs (4c) on the NSP can be included to aid with this manuever, and can be helpful if the pressure applied, identified as "B" must be slightly back toward the syringe barrel to fully pull the needle pocket (6) away from the needle tip. A reverse force at "A" will then bring the NSP needle pocket back away from the needle tip. The liquid in the syringe can then be removed in an intended fashion by applying pressure to the syringe plunger head (2). One using the system never has his fingers near the needle tip.

FIG. 6 shows an overall container comprised of a cap (10) and a container barrel (10a). The entire system apparatus, including a pre-use needle guard (9) will arrive at the location at which use will be made of the system, is a totally sterile fashion. Present packaging exposes the pre-use needle guard to the external environment. The needle is kept sterile, but the pre-use needle guard, which is often times removed from a needle and placed in a sterile setting, is contaminated on its exterior.

Color coding of the container (10) and (10a) will be used to identify needle lengths and/or gauges and/or syringe volume capacity, etc.

It is to be noted that the present system requires that different length NSP's be used with different length needles. This is necessary so coordinated action can occur between the needle pocket (6) on the NSP, and the spring developed by the action of a widened NSP shank (4a) near the NSP head (4) attempting to enter the guide (5). For this reason, and for the reason that the syringe and needle are intended for one time use only; this embodiment utilizes a permanently attached needle and coordinated NSP. Users will not be able to change needles, and perhaps use one of a different length than was originally provided, and re-use the system, in this embodiment's construction. The guide (5) can be specially fabricated into a syringe barrel, or manufactured separately and attached thereto.

Referring now to FIG. 7, it will be appreciated that the elements of a second embodiment of the invention are shown. The major difference from the first embodiment is found in the attachment of the guide (15) to an assembly (20) comprising the guide (15), a needle (13) and means (23) for connecting the assembly to a syringe barrel (11), at the location numbered (21). Said connection means typically comprise screw threads, in standard syringes.

FIG. 8 shows the NSP of the second embodiment (i.e., (14), (14a), (14b), (16) and (17)) which slides into guide (15), securing a needle (13) in the needle securing pocket (16) region. The assembly (20), as described above, is shown attached to a syringe barrel (11).

FIG. 9 shows the configuration in FIG. 8 placed into the top of a container (30). The container is shown in cross section. FIG. 10 provides a top view of the container (30) and in particular shows that the hole (31) into which the assembly (20) is inserted in FIG. 8 is of a shape such that the assembly (20) is unable to rotate about an axis perpendicular to the top of the container and in line with the axis of the hypodermic syringe barrel. It will, hence, be appreciated that if the barrel (11) of the syringe is rotated, the assembly (20) will be removed from the barrel (11) of the syringe, and fall into the container (30) where it can be safely stored. Hence, the second embodiment provides the convenience associated with use of the first embodiment, but in addition allows for safe easy disposal of secured needles after use. Packaging for the second embodiment will be essentially the same as for the first embodiment.

It should be obvious from the foregoing that the present invention provides a combination of features not available in any other known prior invention.

Having hereby disclosed the subject matter of this invention, it should be obvious that many modifications, substitutions and variations of the present invention are possible in light of the teachings. It is, therefore, to be understood that the invention may be practiced other than as specifically described and should be limited in breadth and scope only by the claims.

I claim:

1. A system for securing a hypodermic syringe and needle after use, to prevent accidental pricking of patients or medical professionals, etc., and to prevent unintended leakage of fluid from the syringe portion of the hypodermic through a needle comprising in combination with a hypodermic syringe barrel, an assembly, which assembly comprises a needle, a guide, and means for attachment to the hypodermic syringe barrel; which guide provides an internal space into which a needle securing plunger can slide; which needle securing plunger, at the syringe end, thereof, has a head portion suitable for application of pressure by a user's thumb or finger, etc., followed by, as the length of the needle securing plunger is transversed, a tapering width dimension, which width dimension, becomes a smaller constant width as one follows the needle securing plunger toward the distal needle end thereof, which constant width is slightly smaller than the width of the space in the guide so that the needle securing plunger can slide into said guide; which guide and needle securing plunger further comprise teeth on the outer side of the needle securing plunger and on the inner side of the guide so that when the needle securing plunger is slid into the guide the teeth thereon move past the teeth in the guide, so that the needle securing plunger will not thereafter easily slide back out of the guide; which needle securing plunger further comprises, at the distal end thereof, a needle pocket on the bottom side thereof and a "v" shaped needle guide structure as viewed from the top or bottom of the needle guide structure; and which needle securing plunger is constructed so as to have a natural spring or tendency to curve toward the needle as the needle securing plunger is caused to move through the guide when pressure is applied to the head of the needle securing plunger, so that the needle pocket will naturally move to encompass the needle point as the needle securing plunger is caused to move as just described.

2. A system for securing a hypodermic syringe and needle after use as in claim 1 in which the point at which the needle securing plunger beings to taper into a greater width as the needle securing plunger is transversed from the distal end toward the head of the needle securing plunger, enters the guide as the needle securing plunger is caused to move by the application of pressure on the head of the needle securing plunger by a user's thumb or finger, etc., at the same time the needle pocket encompasses the needle point, so that the needle securing plunger will have a natural tendency to retract from the guide and thereby firmly secure the needle point in the needle pocket, when said applied pressure is released.

* * * * *